United States Patent [19]
Noda et al.
[11] Patent Number: 4,743,677
[45] Date of Patent: May 10, 1988

[54] CALCITONIN GENE RELATED PEPTIDE DERIVATIVES

[75] Inventors: Toshiharu Noda, Shizuoka; Nobutaka Fujii, Hirakata; Kaoru Morita; Masayuki Hori, both of Shizuoka, all of Japan

[73] Assignee: Toyo Jozo Co., Ltd., Tagata, Japan

[21] Appl. No.: 893,267

[22] Filed: Aug. 5, 1986

[30] Foreign Application Priority Data

Aug. 9, 1985 [JP] Japan ................................ 60-175340

[51] Int. Cl.[4] ................................................ C07K 7/36
[52] U.S. Cl. ................................................ 530/307
[58] Field of Search ........................................ 530/307

[56] References Cited

PUBLICATIONS

Chem. Pharm. Bull., 34, 3914–3918 (1986), Otaka et al.

*Primary Examiner*—Delbert R. Phillips
*Attorney, Agent, or Firm*—Oblon, Fisher, Spivak, McClelland & Maier

[57] ABSTRACT

A peptide represented by the following formula:

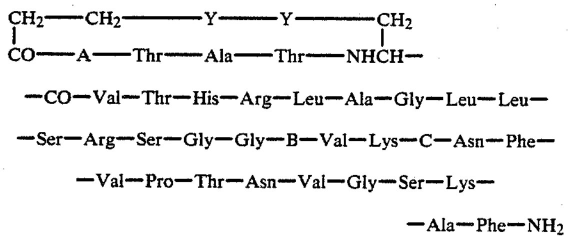

wherein Y means a sulfur atom or methylene group, A stands for Asp or Asn, B denotes Val or Met and C is Asn or Ser, or a salt thereof.

3 Claims, 7 Drawing Sheets

FIG. 1-A
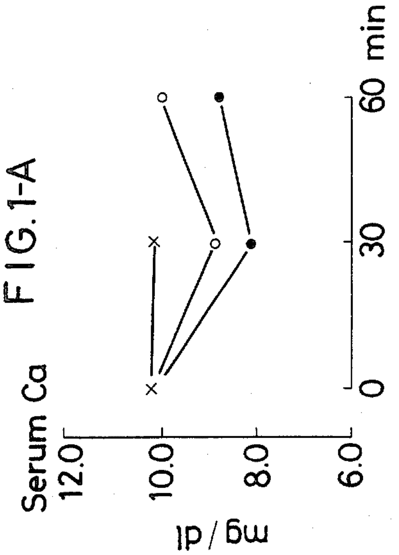
FIG. 1-B
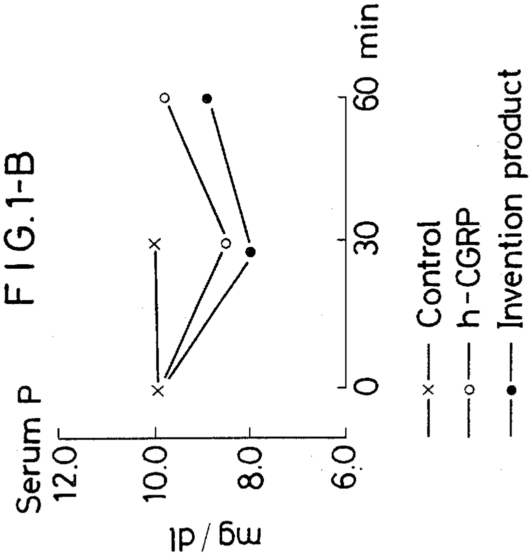
FIG. 2-A
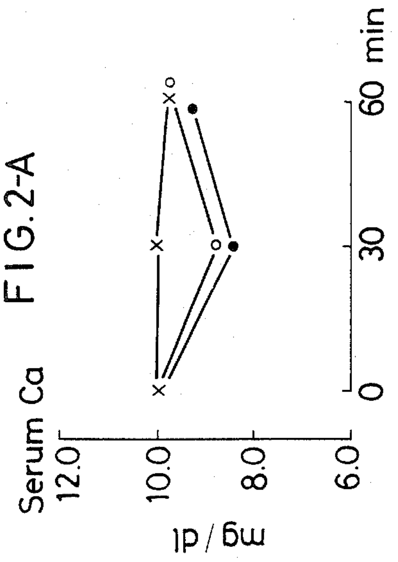
FIG. 2-B
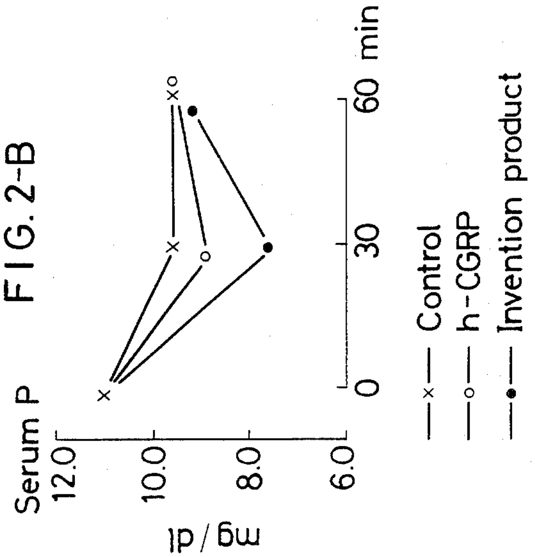

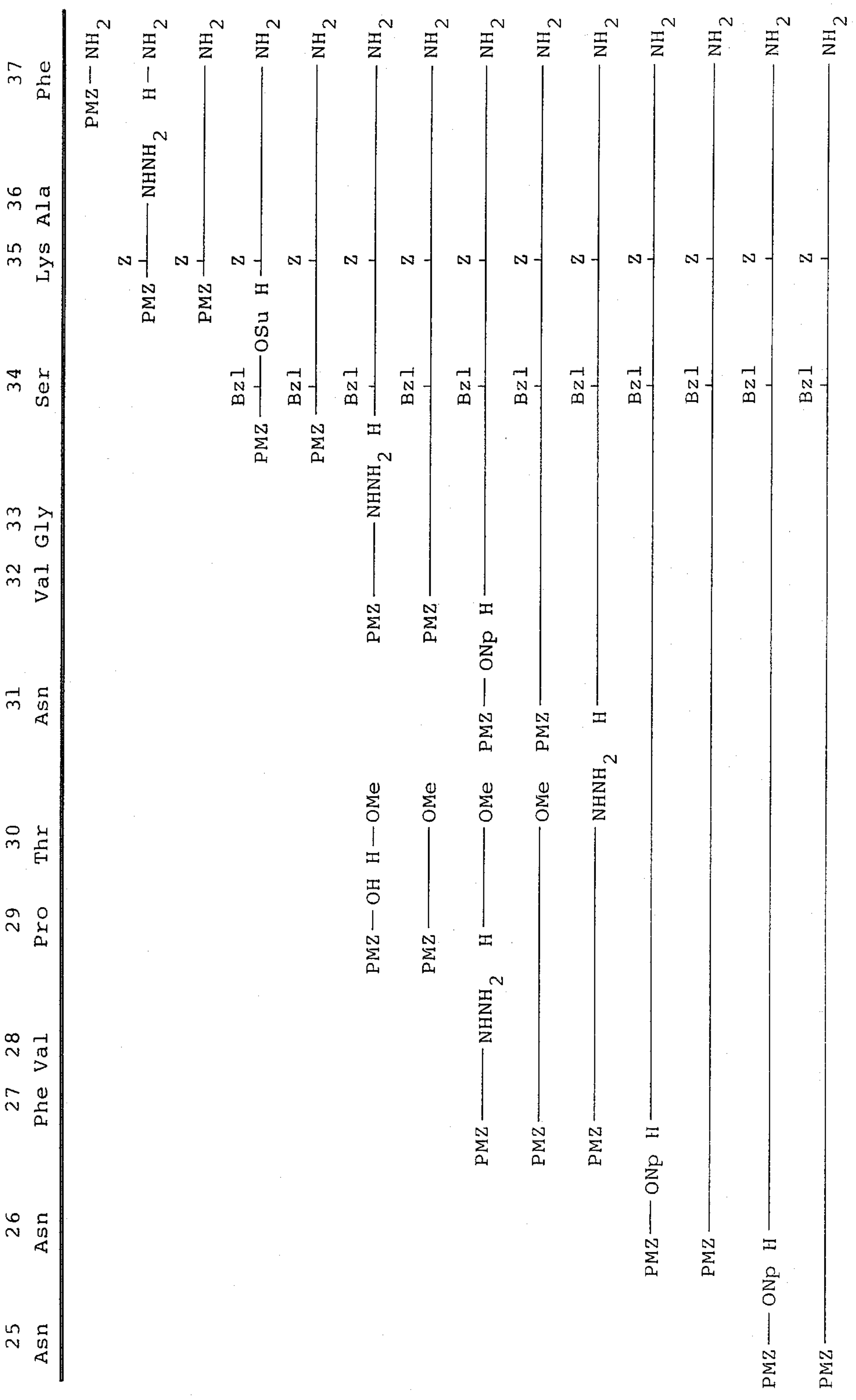

FIG. 3

| 25 | 26 | 27 | 28 | 29 | 30 | 31 | 32 | 33 | 34 | 35 | 36 | 37 |
|----|----|----|----|----|----|----|----|----|----|----|----|----|
| Asn | Asn | Phe | Val | Pro | Thr | Asn | Val | Gly | Ser | Lys | Ala | Phe |

Fragments (reading top to bottom as drawn):

- PMZ—OH  H—OMe (Pro29–Thr30)
- PMZ————OMe (Pro29–Thr30)
- PMZ—NHNH₂  H—OMe (Val28–Thr30, then Asn31)
- PMZ————OMe  PMZ——NH₂ (…–Thr30; Asn31)
- PMZ————————OMe  PMZ (…–Thr30; Asn31)
- PMZ————————NHNH₂  H (…–Asn31)
- PMZ————————————NHNH₂  H (…–Gly33)
- PMZ————————————ONp  H (…–Gly33)
- Bzl  (Ser34)
- PMZ——————Bzl—OSu  H—Z (Ser34–Lys35)
- PMZ——————Bzl————Z (Ser34–Lys35)
- Bzl    Z (Ser34; Lys35)
- PMZ—ONp  H (Asn25–Asn26)
- PMZ———— (Asn25–Asn26)
- PMZ—ONp  H (Asn25)
- PMZ———— (Asn25)

Right-side terminal groups (Lys35 Z; Ala36; Phe37 NH₂) with successive couplings:
- PMZ—NH₂ (Phe37)
- H—NH₂
- ————NH₂
- Z————NH₂
- Z——Bzl————NH₂
- Z——Bzl————NH₂
- Z——Bzl————NH₂
- Z——Bzl————NH₂
- Z——Bzl————NH₂
- Z——Bzl————NH₂
- Z——Bzl————NH₂
- Z——Bzl————NH₂
- Z————————NH₂
- Z————————NH₂
- Z————————NH₂

| 3 | 4 | 5 | 6 | 7——11 | ——17 | 18 | 19——34 | 35——37 |
|---|---|---|---|---|---|---|---|---|
| Asp | Thr | Ala | Cys | Arg | Ser | Arg | Ser | Lys |

```
                PMZ——NHNH₂  H——OMe
         OBzl                                                                                    NH₂
         PMZ——————OMe                                      Adm    Mts    Bzl    Mts    Bzl     Z
         PMZ——ONp  H——————OMe                                                                    NH₂
            OBzl                                           Adm    Mts    Bzl    Mts    Bzl     Z
         PMZ——————OMe
PMB—S—(CH₂)₂—OSu  H——————OMe
PMB—S—(CH₂)₂—CO——————————OMe
PMB—S—(CH₂)₂—CO——————————NHNH₂  H
PMB—S—(CH₂)₂—CO—————————————————————————————————————————————————————
```

CALCITONIN GENE RELATED PEPTIDE DERIVATIVES

BACKGROUND OF THE INVENTION

1. Field of the Invention

This invention relates to novel human calcitonin gene related peptides (hereinafter called "h-CGRPs") useful as medicines or clinical diagnostic aids for bone metabolism and the central nervous system.

2. Discussion of the Background h-CGRPs have been known to have an amino acid sequence represented by the following formula:

```
       ┌─────S─────────S─────┐
H—Ala—Cys—A—Thr—Ala—Thr—Cys—Val—Thr—
—His—Arg—Leu—Ala—Gly—Leu—Leu—Ser—Arg—
—Ser—Gly—Gly—B—Val—Lys—C—Asn—Phe—Val—
—Pro—Thr—Asn—Val—Gly—Ser—Lys—Ala—Phe—NH2
```

wherein A means Asp or Asn, B stands for Val or Met and C denotes Asn or Ser, and various biological properties [Nature, 308(19), 746–748 (1984); FEBS Letters, 183(2), 403 (1985); Neuropeptides, 4, 425–434 (1984); Nature 313(3), 54–56 (1984)].

h-CGRPs are however believed to be subjected to aminopeptidase enzymolysis and hence to undergo progressive deactivation in living bodies since their N-terminal amino groups are not protected. There is thus an outstanding demand for the development of their derivatives which can withstand the enzymolysis by the enzyme and have still stronger biological activities.

SUMMARY OF THE INVENTION

An object of this invention is to provide h-CGRP derivatives which can withstand aminopeptidase enzymolysis and have biological activities stronger than h-CGRPs.

The present invention has now been completed as a result of various researches conducted with a view toward overcoming the above-described drawback. It hence provides novel h-CGRP derivatives having serum calcium and phosphorus level lowering activities stronger than h-CGRPs and moreover, excellent long-acting properties as to development of the activities.

Namely, the present invention provides a peptide represented by the following formula [1]:

```
CH2——CH2——Y——Y——CH2                              [1]
|                 |
CO—A—Thr—Ala—Thr—NHCH—CO—Val—Thr—His—
—Arg—Leu—Ala—Gly—Leu—Leu—Ser—Arg—Ser—
—Gly—Gly—B—Val—Lys—C—Asn—Phe—Val—Pro—
—Thr—Asn—Val—Gly—Ser—Lys—Ala—Phe—NH2
```

wherein Y means a sulfur atom or methylene group, A stands for Asp or Asn, B denotes Val or Met and C is Asn or Ser, or a salt thereof.

The peptide [1] of this invention have stronger serum calcium and phosphorus level lowering effects compared with h-CGRP and moreover, the former are superior in the long-lasting property of activity development. They are hence useful as therapeutic medicines for bone diseases and diseases related to the central nervous system or as clinical diagnostic aids.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1B diagrammatically illustrate the effects of h-CGRP and desalanyl-deamino-h-CGRP of this invention on the serum calcium and inorganic phosphorus levels in rat;

FIGS. 2A and 2B diagrammatically illustrate the effects of h-CGRP and desalanyl-8 $Asu^{2,7}$]-h-CGRP of this invention on the serum calcium and inorganic phosphorus levels in rat;

FIG. 3 is a flow chart for the preparation of the peptide fragment (25–37);

DETAILED DESCRIPTION OF THE PREFERRED EMBODIMENTS

Figure 4:
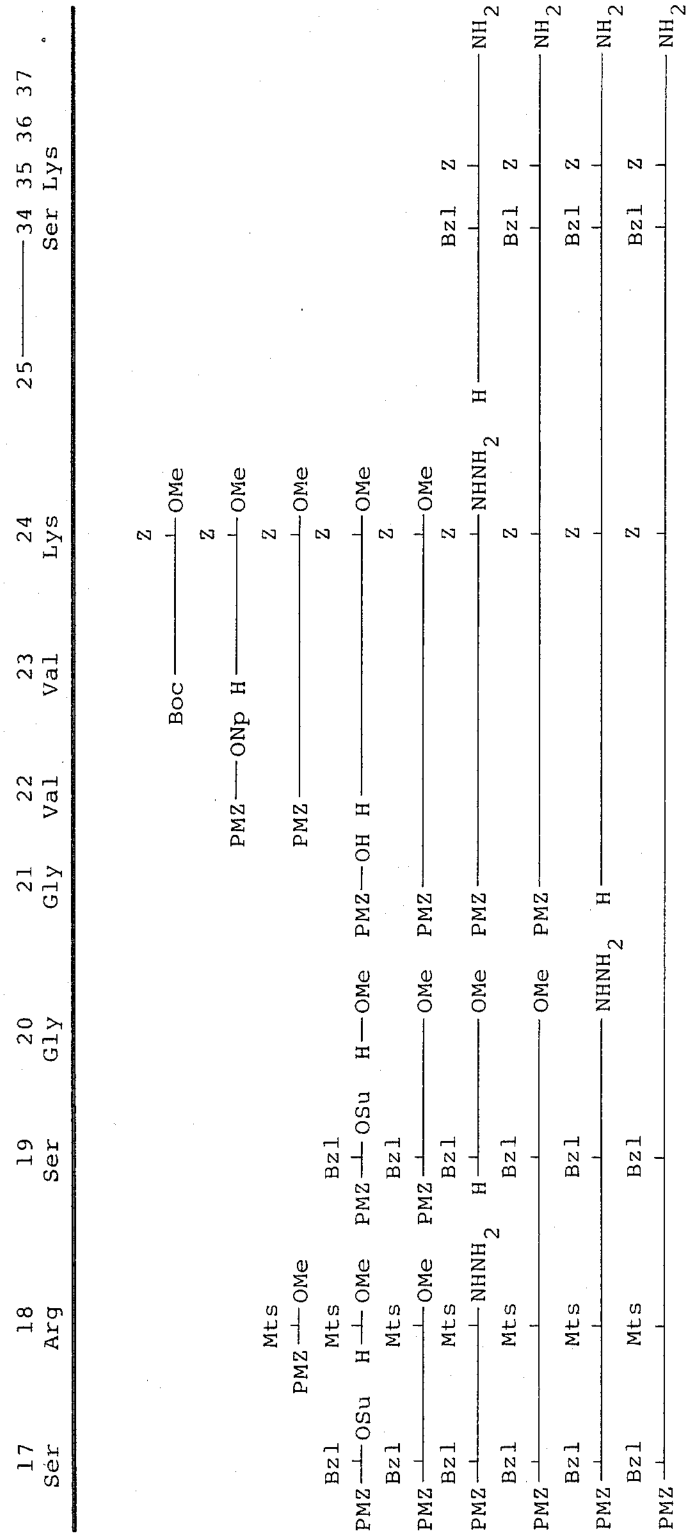
FIG. 4 is a flow chart for the preparation of the peptide fragment (17–37)

In the present invention, a peptide [1] in which Y, A, B and C are a sulfur atom, Asp, Val and Asn respectively may be called "desalanyl-deamino-h-CGRP", another peptide [1] in which Y, A, B and C are a sulfur atom, Asn, Met and Ser respectively may be called "desalanyl-deamino-h-CGRPII", a further peptide [1] in which Y, A, B and C are a methylene group, Asp, Val and Asn respectively may be called "desalanyl-[$Asu^{2,7}$]-h-CGRP", and a still further peptide [1] in which Y, A, B and C are a methylene group, Asn, Met and Ser respectively may be called "desalanyl-[$ASU^{2,7}$]-h-CGRPII"

The polypeptides [1] of this invention can be synthesized by processes well known for the syntheses of polypeptides in the art. When the liquid phase technique is employed, they may for example be obtained in the following manner. Namely, the carboxyl group of the C-terminal phenylalanyl group is converted to an amido group and individual protected amino acids and/or protected lower peptides are condensed together in the amino acid sequence represented by the formula [1]. When Y means a sulfur atom, the protecting group of the β-mercaptopropionyl group acylated to the amino group of the aspartic acid, the N-terminal amino acid, the protecting group of the mercapto group of the L-cysteinyl group and the protective groups of functional groups in other side chains are removed by acid decomposition in the final stage of the condensation reaction, followed by oxidation of the mercapto groups to form a disulfide bridge. When Y means a methylene group, a structural unit formed in a desired stage of the reaction and containing a partial sequence of the following formula:

$$-A-Thr-Ala-Thr-NH\overset{(CH_2)_5COOR}{\overset{|}{C}}HCO-$$

wherein R means an active ester residual group and A has the same meaning as defined above is subjected to a cyclyzing reaction and the protective groups of active groups are removed by acid decomposition in the final stage of the condensation reaction.

The condensation reaction can itself be carried out by repeating the removal of each protecting group and the subsequent condensation reaction in accordance with the routine practice for the syntheses of peptides. Namely, as various protecting groups useful in the production of starting materials and all intermediates for the peptides [1] of the present invention, protecting groups known in the syntheses of peptides, for example, protecting groups readily removable by known methods such as hydrolysis, acid decomposition, reduction, aminolysis or hydrogenolysis may be employed. Such protecting groups are disclosed in literature and textbooks in the field of peptide synthesis chemistry.

In the present invention, it is preferred to use a t-butyloxycarbonyl, benzyloxycarbonyl or p-methoxybenzyloxycarbonyl group for the protection of each α-amino group, a benzyloxycarbonyl or p-chlorobenzyloxycarbonyl group for the protection of an amino group in the side chain, namely, the ε-amino group of lysine, a methyl ester group or benzyl ester group for the protection of each α-carboxyl group, a benzyl ester group for the protection of the side chain carboxyl group of aspartic acid, a t-butyl ester group for the protection of the side chain carboxyl group of α-aminosuberic acid, benzyl groups for the protection of the hydroxyl groups of serine and threonine, and a mesitylene-2-sulfonyl or tosyl group for the protection of the amino group in the guanidyl group of arginine.

In the syntheses of the peptides [1] of this invention, the condensation of each individual amino acid and/or lower peptide may be effected, for example, by reacting an amino acid or lower peptide containing activated terminal α-carboxyl group with an amino acid, or lower peptide containing a free α-amino group and a protected carboxyl group, or by reacting an amino acid or lower peptide containing an activated α-amino group and a protected terminal carboxyl group with an amino acid or lower peptide containing a free terminal α-carboxyl group and a protected amino group.

In the above-described condensation, the carboxyl group can be activated, for example, by converting it into an acid azide, an acid anhydride, an acid imidazolide, or an active ester such as a cyanomethyl ester, p-nitrophenyl ester, N-hydroxysuccinimido ester or the like. Alternatively, the activation may also be effected by conducting the reaction in the presence of a condensing agent, for example, a carbodimide such as N,N'-dicyclohexylcarbodiimide (DCC), N-ethyl-N'-3-dimethylaminopropylcarbodiimide or N,N'-carbonyldiimidazole.

In the present invention, the azide process, active ester process, mixed acid anhydride process and carbodiimide process may be mentioned as preferable condensation processes. It is desirable to use a condensation process capable of avoiding or minimizing racemization in each stage of the condensation. Preferably, the azide process, active ester process, Wünsch process [Z. Naturforsch., 21b, 426 (1966)] or Geiger process [Chem. Ber., 103, 788 (1970)] is used.

Regarding the condensation order, the synthesis can be carried out in any order so long as the amino acid sequence [1] is provided. It is however preferable to join together amino acids and/or lower peptides from the side of the C-terminus.

In order to obtain the intended peptide [1] from the thus-obtained protected linear peptide, subsequent production steps differ depending whether it is intended to obtain a peptide [1] in which Y is a sulfur atom or a peptide [1] in which Y is a methylene group.

When it is intended to obtain the peptide [1] in which Y is a sulfur atom, it is necessary to obtain the above-described protected linear peptide, namely, a pentatriacontane peptideamide containing protected ω-amino, side-chain carboxyl, hydroxyl, guanidino and mercapto groups and acylated with a β-mercaptopropionyl group at the N-terminal amino group. These protecting groups are removed, preferably in a single step by acid decomposition, for example, with trifluoromethanesulfonic acid or anhydrous hydrogen fluoride, thereby obtaining a pentatriacontane peptideamide containing free mercapto groups. Upon oxidation, a disulfide bridge is formed in the peptideamide so that the intended peptide [1] in which Y is a sulfur atom is obtained. The formation of this disulfide bridge is usually carried out by effecting the oxidation with atmospheric oxygen in water, iodine in glacial acetic acid, iodoethane in an organic solvent, or the like.

When it is intended to obtain the peptide [1] in which Y is a methylene group, a structural unit containing a partial sequence represented by the following formula:

$$-A-Thr-Ala-Thr-NH\overset{(CH_2)_5COOR}{\overset{|}{C}}HCO-$$

wherein R and A have the same meaning as defined above is subjected to a cyclizing reaction in the synthesizing stage of the protected linear peptide, namely, in a desired stage of the condensation reaction. This cyclization is effected through a condensation reaction between the ω-carboxyl group of α-aminosuberic acid activated in the above-described manner and the free amino group of the N-terminal amino acid. It is preferable to protect the hydroxyl group of threonine and the side-chain carboxyl group of aspartic acid before the cyclization.

The thus-obtained cyclic peptide containing α-aminosuberic acid and having active groups, which may be either protected or not protected, and a larger peptide having either protected or unprotected active groups are condensed and when protecting groups are still contained, the protecting groups are then removed.

In the manner described above, there is obtained a pentatriacontane peptideamide containing protected ω-amino, side-chain carboxyl, guanidino and hydroxyl groups. These protecting groups are removed, preferably, in a single step by acid decomposition, for example, with trifluoromethanesulfonic acid, anhydrous hydrogen fluoride or the like, whereby the intended peptide [1] in which Y is a methylene group is obtained.

In the present invention, the peptides [1] may each be synthesized by using partially or wholly a solid-phase peptide synthesizing process besides the above-described liquid-phase peptide synthesizing process.

When a peptide [1] in which Y is a sulfur atom is desired for example, a protected pentatriacontane peptide bound resin is obtained by synthesizing the peptide fragment of from the 3rd to 37th amino acids by the solid phase technique and then converting the N-terminal amino group into a mercaptopropionyl group. These protective groups and resin can be removed in a single step by a method well known in the art, for example, with trifuoromethanesulfonic acid, anhydrous hydrogen fluoride or the like, so that a pentatriacontane peptideamide containing free mercapto groups is obtained. The intended peptide [1] in which Y is a sulfur atom is obtained by forming a disulfide bridge in the peptideamide in the same manner as in the above-described liquid phase technique.

When a peptide [1] in which Y is a methylene group is desired on the other hand, a protected pentatriacontane peptide bound resin is obtained, for example, by synthesizing the peptide fragment of from the 9th to 37th amino acids by the solid phase technique, synthesizing a cyclic peptide fragment containing α-aminosuberic acid as an N-terminus by the liquid phase technique, and then condensing the two peptide fragments by the solid phase technique. These protective groups and resin can be removed in a single step by a method well known in the art, for example, with trifluoromethanesulfonic acid, anhydrous hydrogen fluoride or the like, so that the intended peptide [1] in which Y is a methylene group is obtained.

As resins useful in the above-described solid phase technique, may be mentioned resin employed routinely in the solid phase technique, for example, benzhydrylamine resin, p-methylbenzhydrylamine resin, etc. These resins are available as resins having desired properties by choosing different equivalents of functional groups and crosslinking degrees. Commercial products are also available.

In the above-described solid phase technique, the C-terminal amino acid to the 3rd amino acid (when Y is a sulfur atom) or to the 9th amino acid (when Y is a methylene group) are condensed successively one at once to the resin in accordance with the amino acid sequence represented by the formula [1] . The functional groups of the amino acids are protected by a method well known in the art. As examples of such protecting groups, the above-mentioned protecting groups may be mentioned.

Upon the above-described solid-phase reaction, a resin is placed in a reactor, followed by an addition of dichloromethane, chloroform, dimethylformamide, benzene or a solvent capable of causing the resin to swell in an amount of 2–20 ml per gram of the resin. On the side, Boc-amino acid in an amount of 1–6 equivalents per equivalent of the amino groups in the resin is reacted with DCC in a separate reactor, and the resulting symmetrical acid anhydride is separated from by-produced dicyclohexyl urea (DCU) and is then charged in the former reactor in which the above resin is contained. The condensing agent (DCC) may be used in an amount of 0.5–3 equivalents per equivalent of the Boc-amino acid. The reaction is generally conducted for 5–60 minutes.

A portion of the Boc-amino acid-resin or Boc-peptide-resin obtained in each step is sampled and the coupled amount is then determined by measuring the amount of the reacted Boc-amino acid in the usual manner [T. Fairwell, et al., Biochemistry, 22, 2691 (1983)] .

Boc, the protecting group of the α-amino group, is thereafter removed by an acid such as trifluoroacetic acid and the condensation reaction is then carried out successively. The above-described synthesis of the peptide by the solid phase technique is conducted using an automatic solid-phase synthesizing apparatus. It may however be carried out manually. It is desirable to conduct all of these operations under a nitrogen gas stream.

In the manner described above, the resin with the peptide fragment of from the 3rd or 9th to 37th amino acids bound thereon is obtained. It is then necessary to condense the above-described cyclic peptide fragment, which contains α-aminosuberic acid, on the resin with the peptide fragment of from 9th to 37th amino acids bound thereon.

From the thus-obtained resin with the protected pentatriacontane peptideamide bound thereon, the protective groups and resin are removed in a single step with anhydrous hydrogen fluoride or the like as described above so that a pentatriacontane peptideamide having free mercapto groups or the intended peptide [1] in which Y is a methylene group is obtained. By forming a disulfide bridge in the above-described manner, the intended peptide [1] in which Y is a sulfur atom is obtained from the pentatriacontane peptideamide having the free mercapto groups.

The thus-obtained peptides [1] can be isolated and purified by a method well known for the purification of peptides or proteins. Their isolation and purification can be effected, for example, by gel filtration through a gel filter medium such as Sephadex G-25, Sephadex G-50 or Sephadex LH-20 (all trade marks), by column chromatography on carboxymethylcellulose or another ion exchange resin, high performance liquid chromatography, or the like.

The novel peptides [1] of this invention are obtained in the form of bases or their salts depending on conditions of their preparation processes. For example, they can form salts with known organic acids such as acetic acid.

Incidentally, abbreviations described in this specification have the following meaning:

Phe: L-phenylalanine
Ala: L-alanine
Lys: L-lysine
Ser L-serine
Gly: glycine
Val: L-valine
Asn: L-asparagine
Thr: L-threonine
Pro: L-proline
Arg: L-arginine
Leu: L-leucine
His: L-histidine
Cys: L-cysteine
Asp: L-aspartic acid
Met: L-methionine
Asu: L-α-aminosuberic acid
Boc: t-butyloxycarbonyl
Z: benzyloxycarbonyl
PMZ: p-methoxybenzyloxycarbonyl
Cl-Z: p-chlorobenzyloxycarbonyl
Bzl: benzyl
PMB: p-methoxybenzyl
OSu: N-hydroxysuccinimido ester
ONp: p-nitrophenyl ester
OMe: methyl ester
OBut: t-butyl ester OBzl: benzyl ester
Mts: mesitylene-2-sulfonyl
Adm: 1-adamantyl
TFA trifluoroacetic acid
Ether: diethyl ether
DMF: N,N'-dimethylformamide
DMSO: dimethylsulfoxide
MeOH: methanol
DCM: dichloromethane
DIEA: diisopropylethylamine
HOBt: 1-hydroxybenzotriazole
HMPA: hexamethylphosphorylamide
MBHA resin: p-methylbenzhydrylamine resin

EFFECTS OF THE INVENTION

Serum calcium and phosphorus level lowering effects

<Activity measuring method> h-CGRP, desalanyl-deamino-h-CGRP and desalanyl-[$Asu^{2,7}$]-h-CGRP, each 80 μg, were dissolved in 1 ml of a citrate buffer (pH 6.5) containing 0.1% of bovine serum albumin (hereinafter called "dissolving solution") and then administered to a group of 5–6 Wistar rats (80–90 g) at 80 μg/kg through their tail veins. Upon elapsed time of 30 minutes and 60 minutes, blood samples were collected from their abdominal descending aortas. The serum calcium concentrations were measured by atomic absorption spectrophotometry while the serum phosphorus concentrations were determined the method proposed by Goldenberg et al. [Clin Chem., 12, 871–882 (1966)].

<Results>

When desalanyl-deamino-h-CGRP, an invention product, was administered at 80 μg/kg, both serum calcium and phosphorus concentrations dropped by as much as about 20% compared with a control group (a group to which the dissolving solution was only administered) as illustrated in FIG. 1. Even when compared with a group administered with h-CGRP, the concentrations dropped with significance. In addition, the activity exhibiting time was also prolonged. When desalanyl-[$Asu^{2,7}$], an invention product, was administered at 80 μg/kg on the other hand, both serum calcium and phosphorus concentrations dropped by as much as about 20% compared with the control group (the group to which the dissolving solution was only administered) as illustrated in FIG. 2. Even when compared with the h-CGRP administered group, the concentrations dropped with significance.

As has been described above, the peptides [1] of this invention have stronger serum calcium and phosphorus level lowering effects compared with h-CGRP and moreover, the former are superior in the longlasting property of activity development. They are hence useful as therapeutic medicines for bone diseases and diseases related to the central nervous system or as clinical diagnostic aids. Especially, desalanyl-($Asu^{2,7}$)-h-CGRP has extremely good stability in an aqueous solution and when formulated into medicinal preparations, can provides advantageous preparations.

Having generally described this invention, a further understanding can be obtained by reference to certain specific examples which are provided herein for purpose of illustration only and are not intended to be limiting unless otherwise specified.

EXAMPLES

Illustrative preparation of this invention will hereinafter be described specifically in the following examples, in which PF( ) means a peptide fragment of the sequence of amino acids the number of which is indicated in the parentheses.

In the Examples, the following carrier and developers were used in thin-layer chromatography (TLC) and the following hydrolysis conditions were employed for the analysis of amino acids, unless otherwise specifically indicated.

<TLC>

Carrier:

Silica gel ["Art 5715" (trade mark); product of Merck & Co., Inc.].

Developers:

1: chloroform-methanol-water (8:3:1)
2: chloroform-methanol-water (9:1:0.5)
3: butanol-acetic acid-pyridine-water (4:1:1:2)
4: chloroform-methanol-acetic acid (95:5:3)
5: chloroform-methanol-acetic acid (85:15:5)

<Hydrolysis conditions>

Each sample was hydrolyzed at 110° C. for 24–48 hours with 6N hydrochloric acid in a sealed tube.

Example 1

Preparation of Desalanyl-Deamino-h-CGRP

To 6.58 ml of 1M trifluoromethanesulfonic acid-thioanisole/TFA, were added under ice cooling 80 mg (0.0165 mmole) of desalanyl-deamino-protected polypeptide amide (3–37), namely, PMB-S-$(CH_2)_2$-CO-Asp-(OBzl)-Thr-Ala-Thr-Cys(Adm)-Val-Thr-His-Arg (Mts)-Leu-Ala-Gly-Leu-Ser-(Bz)-Ary-(Mts)-Ser (Bz)-Aly-Aly-Val-Val-Lys -Asn-Asn-Phe-Val-Pro-Thr-Asn-Val-Gly-Ser(Bzl)-Lyz(Z)-2 and 344 μl m-cresol, followed by stirring at 0° C. for 2 hours. After the reaction, hexane was added to conduct a solvent treatment and the solvent was then removed by decantation. This procedure was repeated twice and $Et_2O$ was thereafter added to convert the reaction product into powder. The powder was collected by centrifugation and the upper layer, i.e., ether layer was removed. The powder was dried under reduced pressure for 1 hour over KOH. The thus-dried powder was dissolved under ice cooling in about 4 ml of 0.1M Tris-HCl buffer (pH 8.0) in 6 M of guanidine hydrochloride. After addition of 0.2 ml of β-mercaptoethanol, the solution was adjusted to pH 8.0 with 5% methylamine and then stirred at room temperature for 24 hours under an argon gas stream.

The reaction solution was charged in a column (2.8×138 cm) of Sephadex G-25, followed by elution with 1N acetic acid to conduct gel filtration. The eluate was fractionated 9 ml by 9 ml. These fractions were monitored by measuring their absorbances at 206 nm, whereby main fractions (47th–70th) were combined. The solution was diluted with water which had been bubbled with argon gas and chilled with ice. After adjusting its pH to 7.5 with 5% aqueous ammonia, the volume of the solution was brought to about 1 l. It was left over at 23° C. for 1 week to oxidize the reaction product with air.

The reaction mixture was then acidified to pH 5.0 with acetic acid and lyophilized. This lyophilizing procedure was repeated until ammonium acetate was no longer traced, thereby obtaining 40.2 mg of a crude product. The crude product was dissolved in 1M acetic acid in an amount as little as possible. The resulting solution was charged in a column (2×7 cm) of CM-Biogel A (trade name), followed by elution with a 0.02M aqueous solution of ammonium acetate (pH 5.8). The eluate was fractionated 4 ml by 4 ml. After eluting to the 48th fraction, the column was subjected to gradient elution with a linear concentration gradient of 250 ml of a 0.02M aqueous solution of ammonium acetate (pH 5.8)—250 ml of a 0.2M aqueous solution of ammonium acetate (pH 6.8). The eluate was fractionated 4 ml by 4 ml. These fractions were monitored at 750 nm by the Folin-Lowry method to collect main fractions (69th–84th). They were lyophilized to obtain 16.1 mg of desalanyl-deamino-h-CGRP (yield: 40.0%). It was then purified by high performance liquid chromatography under the following conditions to obtain it in a purified form.

Column: Nucleosil$_5$C$_{18}$

Buffer: 0.1% TFA-acetonitrile (gradient elution in which the proportion of acetonitrile was changed over 20–40% in 30 minutes).

Flow rate: 2.5 ml/min.

Fractionation: A peak eluted at about 22 minutes was collected to obtain desalanyl-deamino-h-CGRP.

pI 10.25 or greater.

$[\alpha]_D^{24.5}$: −62.92° (c=0.089, 0.1M acetic acid).

Amino acid analysis: Asp 4.25 (4), Thr 3.58 (4), Ser 2.55 (3), Pro 0.95 (1), Gly 4.20 (4), Ala 3.30 (3), Val 4.57 (5), Leu 2.92 (3), Phe 2.00 (2), Lys 1.93 (2), His 1.16 (1), Arg 1.93 (2).

Figure 5:
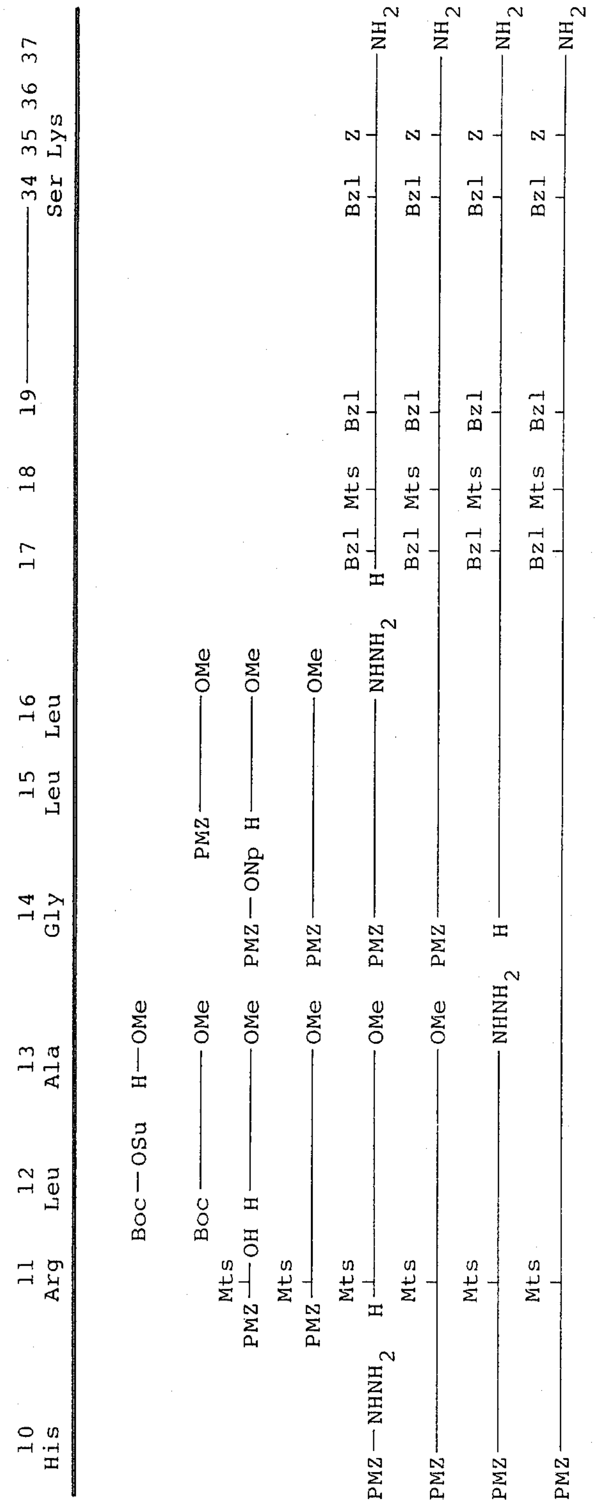
FIG. 5 is a flow chart for the preparation of the peptide fragment (10–37)
Figure 6:
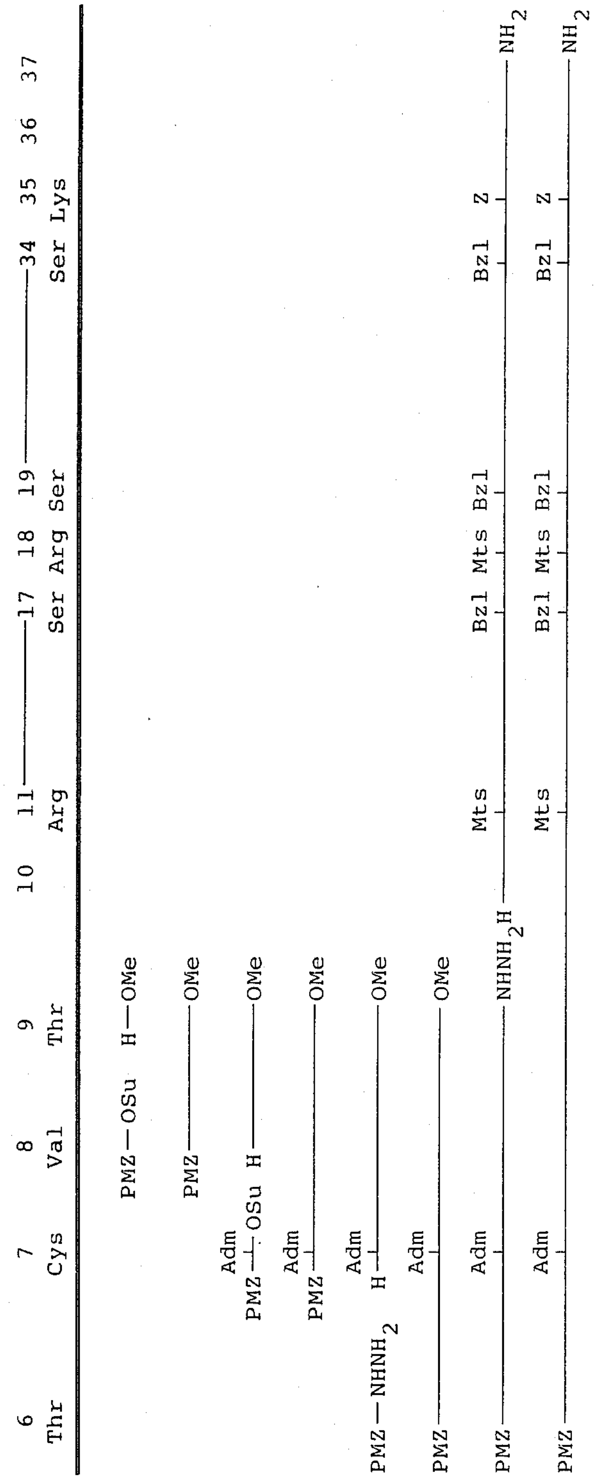
FIG. 6 is a flow chart for the preparation of the peptide fragment (6–37)
Figure 7:
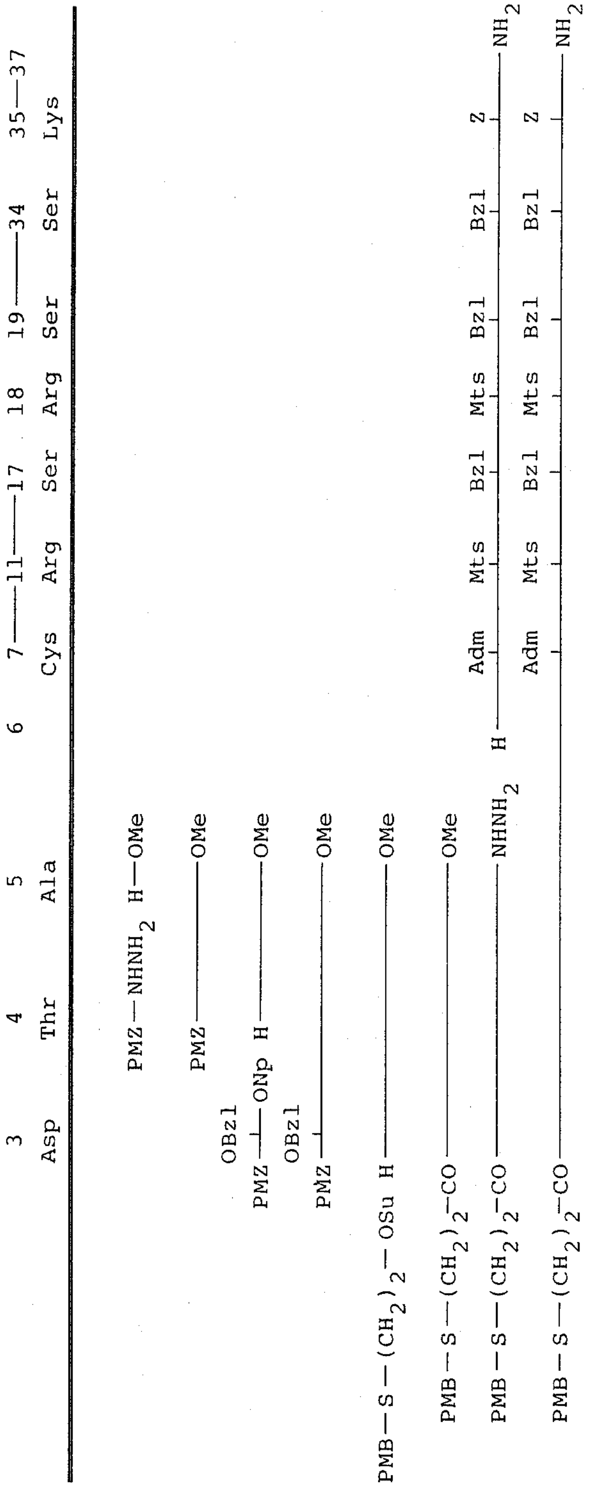
FIG. 7 is a flow chart for the preparation of the peptide fragment (3–37)

The above-described desalanyl-deamino-protected peptide (3–37) was prepared in accordance with the flow chart (FIG. 3) for the preparation of the peptide fragment (25–37), the flow chart (FIG. 4) for the preparation of the peptide fragment (17–37), the flow chart (FIG. 5) for the preparation of the peptide fragment (10–37), the flow chart (FIG. 6) for the preparation of the peptide fragment (6–37) and the flow chart (FIG. 7) for the preparation of the peptide fragment (3–37). Incidentally, the intermediate peptide fragments in the course of the preparation had the following physical and chemical properties.

(1) PF(35–37): PMZ - Lys(Z) - Ala - Phe - NH$_2$.

TLC: Rf$_1$=0.72.

Melting point: 239°–242° C.

Elemental analysis: Calculated for $C_{35}H_{43}N_5O_8$: C,63.52; H,6.55; N, 10.58. Found: C, 63.45; H, 6.58; N, 10.47.

(2) PF(34–37): PMZ - Ser(Bzl) - Lys(Z) - Ala - Phe -NH$_2$.

TLC: Rf$_1$=0.69.

Melting point: 209°–211° C.

$[\alpha]_D^{18}$−8.2° (c=0.86, DMF).

Elemental analysis: Calculated for $C_{45}H_{54}N_6O_{10}$: C, 64.42; H, 6.49; N, 10.02. Found: C, 64.35; H, 6.49; N, 10.03.

(3) PF(32–37): PMZ - Val - Gly - Ser(Bzl) - Lys(Z)- Ala - Phe - NH$_2$.

TLC: Rf$_1$=0.74.

Melting point: 234°–235° C.

$[\alpha]_D^{18}$: −4.2° (c=0.71, DMSO).

Elemental analysis: Calculated for $C_{52}H_{66}N_8O_{12}$: C, 62.76; H, 6.69; N, 11.26. Found: C, 62.70; H, 6.59; N, 11.26.

(4) PF(31–37): PMZ - Asn - Val - Gly - Ser(Bzl) -Lys(Z) - Ala - Phe - NH$_2$.

TLC: Rf$_1$=0.68.

Melting point: 271°–273° C.

$[\alpha]_D^{18}$: −9.6° (c=0.52, DMSO).

Elemental analysis: Calculated for $C_{56}H_{72}N_{10}O_{14}$: C, 60.63; H, 6.54; N, 12.63. Found: C, 60.34; H, 6.54; N, 12.52.

(5) PF(29–30): PMZ - Pro - Thr - OMe.

TLC: Rf$_1$=0.92.

Melting point: 122°–123° C.

$[\alpha]_D^{18}$: −54.2° (c=0.90, MeOH).

Elemental analysis: Calculated for $C_{19}H_{26}N_2O_7$: C, 57.90; H, 6.64; N, 7.10. Found: C, 57.86; H, 6.67; N, 6.98.

(6) PF(27–30): PMZ - Phe - Val - Pro - Thr - OMe.

TLC: Rf$_1$=0.92.

Melting point: 79°–81° C.

$[\alpha]_D^{18}$: −42.1° (c=0.62, MeOH).

Elemental analysis: Calculated for $C_{33}H_{44}N_4O_9$: C, 61.86; H, 6.92; N, 8.75. Found: C, 61.97; H, 7.13; N, 8.58.

(7) PF(27–30): PMZ - Phe - Val - Pro - Thr - NHNH$_2$.

TLC: Rf$_1$=0.61.

Melting point: 138°–139° C.

$[\alpha]_D^{18}$: −44.0° (c=0.77, DMF).

Elemental analysis: Calculated for $C_{33}H_{44}N_6O_8 \cdot \frac{1}{2}H_2O$: C, 59.15; H, 6.98; N, 12.94. Found: C, 59.34; H, 6.84; N, 12.93.

Amino acid analysis: Thr 1.01, Pro 1.28, Val 1.00, Phe 1.11.

(8) PF(27–37): PMZ - Phe - Val - Pro - Thr - Asn - Val - Gly - Ser(Bzl) - Lys(Z) - Ala - Phe - NH$_2$.

TLC: Rf$_1$=0.56.

Melting point: 276°–278° C.

$[\alpha]_D^{18}$: −21.8° (c=0.55, DMSO).

Elemental analysis: Calculated for $C_{79}H_{104}N_{14}O_{19} \cdot \frac{1}{2}H_2O$: C, 60.71; H, 6.77; N, 12.55. Found: C, 60.58; H, 6.59; N, 12.88.

Amino acid analysis: Asp 1.05, Thr 0.93, Ser 0.97, Pro 1.12, Gly 1.07, Ala 1.13, Val 1.84, Phe 2.00, Lys 1.06.

(9) PF(26–37): PMZ - Asn - Phe - Val - Pro - Thr - Asn - Val - Gly - Ser(Bzl) - Lys(Z) - Ala - Phe - NH$_2$.

TLC: Rf$_1$=0.49.

Melting point: 273°–275° C.

$[\alpha]_D^{18}$: −22.7° (c=0.53, DMSO).

Elemental analysis: Calculated for $C_{83}H_{110}N_{16}O_{21} \cdot H_2O$: C, 59.13; H, 6.70; N, 13.29. Found: C, 59.10; H, 6.49; N, 13.31.

(10) PF(25–37): PMZ - Asn - Asn - Phe - Val - Pro - Thr - Asn - Val - Gly - Ser(Bzl) - Lys(Z) - Als - Phe - NH$_2$.

TLC Rf$_1$=0.41.

Melting point; 276°–277° C.

$[\alpha]_D^{18}$: −22.4° (c=0.63, DMSO).

Elemental analysis: Calculated for $C_{87}H_{116}N_{18}O_{23}$ $H_2O$: C, 58.04; H, 6.61; N, 14.01. Found: C, 57.88; H, 6.54; N, 14.18.

Amino acid analysis Asp 3.15, Thr 0.97, Ser 1.04, Pro 1.10, Gly 1.05, Ala 1.08, Val 1.87, Phe 2.00, Lys 1.13.

(11) PF(23–24): BOC - Val - Lys(Z) - OMe

TLC: Rf$_1$=0.60.

Melting point 95.5°–97° C.

$[\alpha]_D^{25}$: −21.0° (c=1.0, MeOH).

Elemental analysis Calculated for $C_{25}H_{39}N_3O_7$: C, 60.83; H, 7.97; N, 8.51. Found: C, 60.52; H, 8.05; N, 8.90.

(12) PF(22–24): PMZ - Val - Val - Lys(Z) - OMe

TLC: Rf$_1$=0.90.

Melting point: 210.5°–213° C.

$[\alpha]_D^{25}$: −1.0° (c=1.0, DMF).

Elemental analysis Calculated for $C_{34}H_{48}N_4O_9$: C, 62.18; H, 7.37; N, 8.53. Found: C, 61.92; H, 7.53; N, 8.49.

(13) PF(21–24): PMZ - Gly - Val - Val - Lys(Z) - OMe

TLC: Rf$_1$=0.83.

Melting point: 191°-194° C.

$[\alpha]_D^{25}$: −4.0° (c=4.0, DMF).

Elemental analysis Calculated for $C_{36}H_{51}N_5O_{10}H_2O$: C, 59.08; H, 7.39; N, 9.57. Found: C, 59.48; H, 7.35; N, 9.56.

(14) PF(21-24): PMZ - Gly - Val - Val - Lys(Z) - $NHNH_2$.

TLC: $Rf_1$=0.59.

Melting point: 232°-236° C.

$[\alpha]_D^{25}$: −7.5° (c=1.1, DMF).

Elemental analysis: Calculated for $C_{35}H_{51}N_7O_9$: C, 58.89; H, 7.20; N, 13.74. Found: C, 58.67; H, 7.50; N, 13.71.

Amino acid analysis GLy 1.0, Val 1.59, Lys 1.02.

(15) PF(17-18): PMZ - Ser(Bzl) - Arg(Mts) - OMe.

TLC: $Rf_1$=0.71.

Melting point 58°-61° C.

$[\alpha]_D^{25}$: −3.3° (c=0.9, MeOH).

Elemental analysis Calculated for $C_{35}H_{45}N_5O_9S$: C, 59.05; H, 6.37; N, 9.84. Found: C, 59.30; H, 6.58; N, 9.90.

(16) PF(17-18): PMZ - Ser(Bzl) - Arg(Mts) - $NHNH_2$.

TLC: $Rf_1$=0.66.

Melting point: 166°-167° C.

$[\alpha]_D^{18}$: −34.0° (c=1.0, MeOH).

Elemental analysis Calculated for $C_{34}H_{45}N_7O_9S$: C, 57.37; H, 6.37; N, 13.78. Found: C, 57.32; H, 6.37; N, 13.70.

(17) PF(19-20): PMZ - Ser(Bzl) - Gly - OMe.

TLC: $Rf_1$=0.81.

Melting point: 84°-86° C.

$[\alpha]_D^{18}$: 1.37° (c=0.73, MeOH).

Elemental analysis Calculated for $C_{22}H_{26}N_2O_7$: C, 61.38; H, 6.09; N, 6.51. Found: C, 61.19; H, 6.13; N, 6.68.

(18) PF(17-20): PMZ - Ser(Bzl) - Arg(Mts) - Ser(Bzl) - Gly - OMe.

TLC: $Rf_1$=0.81.

Melting point: 112°-113° C.

$[\alpha]_D^{25}$: −3.46° (c=0.87, MeOH).

Elemental analysis Calculated for $C_{47}H_{59}N_7O_{12}S$: C, 59.67; H, 6.29; N, 10.36. Found: C, 59.48; H, 6.23; N, 10.53.

(19) PF(17-20): PMZ - Ser(Bzl) - Arg(Mts) - Ser(Bzl) - Gly - $NHNH_2$.

TLC: $Rf_1$=0.76.

Melting point: 134°-136° C.

$[\alpha]_D^{18}$: 1.49° (c=0.67, DMF).

Elemental analysis: Calculated for $C_{46}H_{59}N_9O_{11}S$: C, 58.40; H, 6.29; N, 13.33. Found: C, 58.12; H, 6.20; N, 13.27.

Amino acid analysis Ser 1.89, Gly 1.00, Arg 1.03.

(20) PF(15-16): PMZ - Leu - Leu - OMe.

TLC: $Rf_1$=0.95

(21) PF(14-16): PMZ - Gly - Leu - Leu - OMe.

TLC $Rf_1$=0.96

(22) PF(14-16): PMZ - Gly - Leu - Leu - $NHNH_2$.

TLC: $Rf_1$=0.71

Melting point: 131°-132° C.

$[\alpha]_D^{20}$: −23.0° (c=0.53, DMF).

Elemental analysis Calculated for $C_{23}H_{37}N_5O_6$. C, 57.60; H, 7.78; N, 14.10. Found: C, 57.74; H, 7.73; N, 14.41.

Amino acid analysis: Gly 1.00, Leu 2.01.

(23) PF(12-13): BOC - Leu - Ala - OMe.

TLC: $Rf_1$=0.76

Melting point: 114°-116° C.

$[\alpha]_D^{25}$: −35.0° (c=1.0, MeOH).

Elemental analysis: Calculated for $C_{15}H_{28}N_2O_5$: C, 56.94; H, 8.92; N, 8.85. Found: C, 57.30; H, 9.16;

(24) PF(11-13): PMZ - Arg(Mts) - Leu - Ala - OMe.

TLC: $Rf_1$=0.59

Melting point: 83°-84° C.

$[\alpha]_D^{25}$: −21.0° (c=1.0, MeOH).

Elemental analysis Calculated for $C_{34}H_{50}N_6O_9S$: C, 56.80; H, 7.01; N, 11.69. Found: C, 56.68; H, 7.05; N, 11.36.

(25) PF(10-13): PMZ - His - Arg(Mts) - Leu - Ala -OMe.

TLC: $Rf_1$=0.58

Melting point: 111°-115° C.

$[\alpha]_D^{18}$: 18.0° (c=1.0, MeOH).

Elemental analysis Calculated for $C_{40}H_{57}N_9O_{10}S$ . 3/2 $H_2O$: 54.40; H, 6.85; N, 14.28. Found: C, 54.51; H, 6.62; N, 14.36.

(26) PF(10-13): PMZ - His - Arg(Mts) - Leu - Ala - $NHNH_2$.

TLC: $Rf_1$=0.47

Melting point: 138°-140° C.

$[\alpha]_D^{18}$: −3.79° (c=0.79, DMF).

Elemental analysis: Calculated for $C_{39}H_{57}N_{11}O_S$: C, 53.59; H, 6.80; N, 17.63. Found: C, 53.61; H, 6.77; N, 17.59.

Amino acid analysis His 0.95, Arg 0.99, Leu 0.99, Ala 1.00.

(27) PF(7-9): PMZ - Cys(Adm) - Val - Thr - OMe.

TLC $Rf_1$=0.86

Melting point: 140°-142° C.

$[\alpha]_D^{18}$: −3.31° (c=0.73, MeOH).

Elemental analysis Calculated for $C_{32}H_{47}N_3O_S$: C, 60.64; H, 7.74; N, 6.63. Found C, 60.80; H, 7.48; N, 6.70.

(28) PF(6-9): PMZ - Thr - Cys(Adm) - Val - Thr - OMe.

TLC: $Rf_1$=0.91

Melting point: 219°-221° C.

$[\alpha]_D^{18}$: −25.7° (c=1.01, DMSO).

Elemental analysis: Calculated for $C_{36}H_{54}N_4O_{10}S$: C, 58.83; H, 7.41; N, 7.64. Found: C, 58.85; H, 7.27; N, 7.62.

(29) PF(6-9): PMZ - Thr - Cys(Adm) - Val - Thr - $NHNH_2$.

TLC: $Rf_2$=0.33

Melting point: 239°-240° C.

$[\alpha]_D^{18}$: −7.04° (c=0.99, DMF).

Elemental analysis Calculated for $C_{35}H_{54}N_6O_9S$ .$H_2O$; C, 55.83; H, 7.23; N, 11.46. Found: C, 55.86; H, 7.34; N, 11.40

Amino acid analysis Thr 1.74, Val 1.00, Cys ND.

(30) PF(3-5): PMZ - Asp(OBzl) - Thr - Ala - OMe.

TLC: $Rf_1$=0.89

Melting point: 153°-155° C.

$[\alpha]_D^{18}$: −35.5° (c=0.51, MeOH).

Elemental analysis Calculated for $C_{28}H_{35}N_3O_9$ .½$H_2O$: C, 57.72; H, 6.23; N, 7.21. Found: C, 57.83; H, 6.20; N, 7.28.

(31) PF(3-5): PMZ - S - $(CH_2)_2$ - CO - Asp - Thr - Ala - OMe.

TLC: $Rf_1$=0.5

Melting point: 140°-142° C $[\alpha]_D^{18}$: −10 2° (c=0.6, DMF).

Elemental analysis: Calculated for $C_{23}H_{33}N_3O_9S$: C, 52.36; H, 6.30; N, 7.97. Found: C, 52.09; H, 6.44; N, 7.70.

(32) PF(3-5): PMB - S - (CH ) - CO - Asp - Thr - Ala - $NHNH_2$.

TLC: $Rf_1$=0.21

Amino acid analysis: Asp 1.06 (1), Thr 0.97 (1), Ala 1.00 (1).

(33) PF(21–37): PMZ - Gly - Val - Val - Lys(Z) - Asn -Asn - Phe - Val - Pro - Thr - Asn -Val - Gly - Ser(Bzl) - Lys(Z) - Ala-Phe - $NH_2$.

TLC: $Rf_1=O$, $Rf_3=0$.

Melting point 289°–291° C.

$[\alpha]_D^{18}$: −17.4° (c=0.86, HMPA).

Elemental analysis: Calculated for $C_{113}H_{115}N_{23}O_{29}$: C, 59.02; H, 6.79; N, 14.01. Found: C, 58.72; H, 7.01; N, 14.11.

Amino acid analysis Asp 2.96 (3), Thr 0.93 (1), Ser 0.96 (1), Pro 1.08 (1), Gly 1.99 (2), Ala 1.00 (1), Val 2.54 (3), Phe 2.00 (2), Lys 2.04 (2).

(34) PF(17–37): PMZ - Ser(Bzl) - Arg(Mts) - Ser(Bzl) - Gly - Gly - Val - Val - Lys(Z) - Asn - Asn - Phe - Val - Pro - Thr - Asn - Val - Gly - Ser(Bzl) - Lys(Z) - Ala - Phe - $NH_2$.

TLC: $Rf_1=0.49$.

Melting point: 284°–286° C.

$[\alpha]_D^{18}$: −14.0° (c=0.72, HMPA).

Elemental analysis: Calculated for $C_{150}H_{202}N_{30}O_{37}S$: C, 59.08; H, 6.68; N, 13.78. Found: C, 58.78; H, 6.87; N, 13.68.

Amino acid analysis: Asp 2.92 (3), Thr 0.93 (1), Ser 2.88 (3), Pro 1.13 (1), Gly 2.91 (3), Ala 1.00 (1), Val 2.20 (3), Phe 2.00 (2), Lys 1.95 (2), Arg 0.98 (1).

(35) PF(14–37): PMZ - Gly - Leu - Leu - Ser(Bzl) - Arg(Mts) - Ser(Bzl) - Gly - Gly - Val - Val - Lys(Z) - Asn - Asn - Phe - Val - Pro - Thr - Asn - Val - Gly - Ser(Bzl) - Lys(Z) - Ala - Phe - $NH_2$.

TLC: $Rf_1=0.66$, $Rf_3=0.79$.

Melting point: 284°–287° C.

$[\alpha]_D^{18}$: −22.9° (c=0.53, DMSO).

Elemental analysis Calculated for $C_{164}H_{227}N_{33}O_{40}S$ $.3H_2O$: C, 58.16; H, 6.89; N, 13.65. Found: C, 58.10; H, 7.07; N, 13.71.

Amino acid analysis Asp 2.85 (3), Thr 0.90 (1), Ser 2.89 (3), Pro 1.01 (1), Gly 3.85 (4), Val 2.66 (3), Leu 2.11 (2), Phe 2.00 (2), Lys 1.95 (2), Arg 0.96 (1).

(36) PF(10–37): PMZ - His - Arg(Mts) - Leu - Ala - Gly - Leu - Leu - Ser(Bzl) - Arg(Mts) - Ser(Bzl) - Gly - Gly - Val - Val - Lys(Z) - Asn - Asn - Phe - Val - Pro - Thr - Asn - Val - Gly - Ser(Bzl) - Lys(Z) - Ala - Phe - NH .

TLC: $Rf_1=0.42$, $Rf_3=0.79$.

Melting point: 273°–274° C.

$[\alpha]_D^{18}$: −19.7° (c=0.76, DMSO).

Elemental analysis: Calculated for $C_{194}H_{272}N_{42}O_{46}S_2$ $.14H_2O$: C, 54.89; H, 7.16; N, 13.86. Found: C, 55.05; H, 7.16; N, 13.48.

Amino acid analysis Asp 3.05 (3), Thr 0.93 (1), Ser 2.92 (3), Pro 1.02 (1), Gly 4.30 (4), Ala 2.09 (2), Val 2.82 (3), Leu 3.41 (3), Phe 2.00 (2), Lys 2.10 (2), His 1.04 (1), Arg 2.09 (2).

(37) PF(6–37): PMZ - Thr - Cys(Adm) - Val - Thr - His - Arg(Mts) - Leu - Ala - Gly - Leu - Leu - Ser(Bzl) - Arg(Mts) - Ser(Bzl) - Gly - Gly - Val - Val - Lys(Z) - Asn - Asn - Phe - Val - Pro - Thr - Asn - Val - Gly - Ser(Bzl) - Lys(Z) - Ala - Phe - $NH_2$.

TLC: $Rf_1=0.51$.

Melting point: 300° C. (decomposed).

$[\alpha]_D^{18}$−10.1° (c=0.49, DMSO). Elemental analysis Calculated for $C_{220}H_{314}N_{46}O_{52}S_3$ $.6H_2O$: C, 56.95; H, 7.08; N, 13.89. Found: C, 57.13; H, 7.13; N, 13.61.

Amino acid analysis: Asp 3.18 (3), Thr 2.63 (3), Ser 2.96 (3), Pro 0.93 (1), Gly 4.05 (4), Ala 2.04 (2), Val 4.20 (5), Leu 3.25 (3), Phe 2.00 (2), Lys 2.20 (2), His 1.09 (1), Arg 2.03 (2).

(38) PF(3–37): Desalanyl-deamino-protected peptideamide (3–37).

TLC: $Rf_1=0.42$.

Amino acid analysis: Asp 4.37 (4), Thr 3.78 (4), Ser 3.10 (3), Pro 0.98 (1), Gly 4.33 (4), Ala 3.67 (3), Val 4.36 (5), Leu 3.36 (3), Phe 2.00 (2), Lys 2.01 (2), His 1.00 (1), Arg 2.11 (2).

EXAMPLE 2

Preparation of Desalanyl-[$Asu^{2,7}$]-h-CGRP

Anisole (2 ml) was added to 1.27 g of desalanyl-[$Asu^{2,7}$]-protected-h-CGRP(3–37)-MBHA resin, namely, $CH_2$———$(CH_2)_3$———$CH_2$ CO—Asp—Thr—Ala—Thr—NHCH—CO—Val—Thr(Bzl)—

—His—Arg(Tos)—Leu—Ala—Gly—Leu—Leu—Ser(Bzl)—

—Arg(Tos)—Ser(Bzl)—Gly—Gly—Val—Val—Lys(Cl—Z)—

—Asn—Asn—Phe—Val—Pro—Thr(Bzl)—Asn—Val—Gly—

—Ser(Bzl)—Lys(Cl—Z)—Ala—Phe—MBHA resin.

Then, 15 ml of anhydrous hydrogen fluoride was added to the resulting mixture, followed by stirring at 0° C. for 1 hour. After the reaction, anhydrous hydrogen fluoride was distilled off under reduced pressure and the residue was washed with ether. To the residue, 20 ml of 0.1M acetic acid was added to extract the resulting peptide. The extract was passed through a column (3.2×10 cm) of "Dowex WGR" (trade name) and the column was eluted with 60 ml of 0.1M acetic acid. The thus-obtained eluate was lyophilized to obtain 532 mg of white powder. This powder was charged in a column (2.8×17 cm) of carboxymethylcellulose, followed by gradient elution with a linear concentration gradient of 400 ml of a 0.02M aqueous solution of ammonium acetate (pH 4.8)—400 ml of a 0.2M aqueous solution of ammonium acetate (pH 6.0). The eluate was fractionated 9.5 ml by 9.5 ml. A 100 μl portion of the eluate was stained by the Folin-Lowry method and measured at 750 nm. The 55th–84th fractions were pooled and charged in a column (2.8×15 cm) of "CHP-20 Resin" (trade name; product of Mitsubishi Chemical Industries, Ltd.), followed by gradient elution with a linear concentration gradient of 400 ml of a 0.1M aqueous solution of acetic acid, which contained 20% of acetonitrile,—400 ml of a 0.1M aqueous solution of acetic acid which contained 50% of acetonitrile. The eluate was fractionated 11.4 ml by 11.4 ml and the 18th–26th fractions were pooled. They were lyophilized to obtain 22.4 mg of white powder. The white powder was purified by reversed phase high-performance liquid chromatography (HPLC) under the following conditions, thereby obtaining 10.0 mg of desalanyl-[$Asu^{2,7}$]-h-CGRP in a purified form.

Column: $Nucleosil_5C_{18}$

Buffer: 0.1% TFA-acetonitrile (gradient elution in which the proportion of acetonitrile was changed over 28–38% in 20 minutes).

Flow rate: 2.5 ml/min.

Fractionation: A peak eluted at 14.4 minutes was collected.

Physical properties of the product:

pI 10.25 or greater.

$[\alpha]_D^{24.5}$: −45.97° (c=0.087, 0.1M acetic acid).

Amino acid analysis: Asp 4.08 (4), Thr 3.77 (4), Ser 2.74 (3), Pro 1.12 (1), Gly 4.15 (4), Ala 1 , Val 4.60 (5), Leu 3,20 (3), Phe 2.18 (2), Lys 2.11 (2), His 0.98 (1), Arg 2.10 (2), Asu 1.12 (1).

The above-described desalanyl-[$Asu^{2,7}$]-protected h-CGRP(3–37)-MBHA resin was prepared in the following manner.

Solid phase synthesis was carried out using "430-A Peptide Synthesizer" (trade name; manufactured by Applied Biosystems Inc.) as a solid phase synthesizing apparatus.

(1) Preparation of PF(9–37)-MBHA resin, namely, H - Thr(Bzl) - His - Arg(Tos) - Leu - Ala - Gly - Leu - Leu - Ser(Bzl) - Arg(Tos) - Ser(Bzl) - Gly - Gly - Val - Val - Lys(Cl-Z) - Asn - Asn - Phe - Val - Pro - Thr(Bzl) - Asn - Val - Gly - Ser(Bzl) - Lys(Cl-Z) - Ala - Phe - MBHA resin:

Placed in the solid-phase peptide-synthesizing reaction vessel was 0.8 g of an MBHA resin (product of Applied Biosystems, Inc.; amino groups: 0.61 mmole/g). Under a nitrogen gas stream, the resin was treated successively with 8 ml of DCM (4 times, each, for 1 minute), 8 ml of a DCM solution containing 60% of TFA (20 minutes), 4 ml of DCM (3 times, each, for 15 minute), 3 ml of a DMF solution containing 1 ml of DIEA (twice, each, for 1 minute) and 8 ml of DMF (6 times, each, for 40 seconds) in order with filtration after each treatment.

Two millimoles of Boc-Phe, the 37th amino acid in the amino acid sequence, were dissolved in 5 m; of DCM, followed by an addition of 2 ml of DCC (0.5M DCM solution) in an amino acid activating vessel. They were reacted for 5 minutes. The reaction mixture was filtered and the filtrate was transferred to a condensing vessel. After addition of 3 ml of DMF, DCM was distilled off under a nitrogen gas stream. Three milliliters of DMF was then added to the residue and the resulting mixture was transferred to the above-described reaction vessel, in which they were reacted for 25 minutes. The reaction mixture thereafter washed with 8 ml of DCM (6 times, each, for 20 seconds) and filtered to obtain Boc-Phe-MBHA resin.

The Boc-Phe-MBHA resin was then washed with 8 ml of DCM (4 times, each, for 1 minute) in the reaction vessel. The Boc-Phe-MBHA resin was collected by filtration, followed by an addition of 8 ml of a 40% DCM solution containing 60% of TFA. The resulting mixture was stirred for 20 minutes to remove Boc. The thus-obtained resin was washed successively with 4 ml of DCM (3 times, each, for 15 seconds), 3 ml of a DMF solution containing 1 ml of DIEA (twice, each, for 1 minute) and 8 ml of DMF (6 times, each, for 40 seconds) in order with filtration after each washing On the other hand, 2 mmole of Boc-Ala, the 36th amino acid in the amino acid sequence, was dissolved in 5 ml ml of DCM. In an amino acid activating vessel, 2 ml of DCC (0.5M DCM solution) was added to the resulting solution They were reacted for 5 minutes. Thereafter, the reaction product was treated in the same manner as in the Boc-Phe After addition of DMF and subsequent concentration under a nitrogen gas stream, the resulting concentrate was transferred to a reaction vessel so as to conduct a reaction for 20 minutes. The reaction mixture was then washed with 8 ml of DCM (6 times, each, for 20 seconds) and filtered to obtain Boc-Ala-Phe-resin.

Thereafter, the 35th–9th amino acids were successively coupled to obtain PF(9–37)-MBHA resin. The following protected amino acids were used.

| Amino acid sequence | Protected amino acid | Amount used (mmoles) |
|---|---|---|
| 35 | Boc—Lys(Cl—Z) | 2 |
| 34 | Boc—Ser(Bzl) | 2 |
| 33 | Boc—Gly | 2 |
| 32 | Boc—Val | 2 |
| 31 | Boc—Asn | 2 × 2 |
| 30 | Boc—Thr | 2 |
| 29 | Boc—Pro | 2 |
| 28 | Voc—Val | 2 |
| 27 | Boc—Phe | 2 |
| 26 | Boc—Asn | 2 × 2 |
| 25 | Boc—Asn | 2 × 2 |
| 24 | Boc—Lys(Cl—Z) | 2 |
| 23 | Boc—Val | 2 |
| 22 | Boc—Val | 2 |
| 21 | Boc—Gly | 2 |
| 20 | Boc—Gly | 2 |
| 19 | Boc—Ser(Bzl) | 2 |
| 18 | Boc—Arg(Tos) | 2 × 2 |
| 17 | Boc—Ser(Bzl) | 2 |
| 16 | Boc—Leu | 2 |
| 15 | Boc—Leu | 2 |
| 14 | Boc—Gly | 2 |
| 13 | Boc—Ala | 2 |
| 12 | Boc—Leu | 2 |
| 11 | Boc—Arg(Tos) | 2 × 2 |
| 10 | Boc—His(Tos) | 2 |
| 9 | Boc—Thr(Bzl) | 2 |

When Asn and Arg were used in the above solid-phase phase synthesis, 2 ml of DCC solution and 2 ml of HOBt solution (0.5 M DMF solution) were added to the amino acids (2 mmoles, each) in 4 ml of a 3:1 DMF-DCM mixed solvent. After reacting them for 1 minute, the reaction product was treated in the same manner as done with respect to other amino acids. The resulting mixture was thereafter transferred to a reaction vessel to subject same to a coupling reaction. After washing the reaction mixture with DCM and filtering same, 2 ml of DCC solution and 2 ml of HOBt solution (0.5 M DMF solution) were again added to the amino acids (2 mmoles, each) in 4 ml of a 3:1 DMF-DCM mixed solvent. After reacting them for 25 minutes, the resulting mixture was transferred to a reaction vessel to subject same to a coupling reaction. Namely, the synthesis was conducted by the so-called double coupling process. (2) Preparation of desalanyl-[$Asu^{2,7}$]-protected-h-CGRP(3–37)-MBHA resin:

Dissolved in 8 ml of DMF was 334 mg of the cyclic PF(3–8) [10], namely,

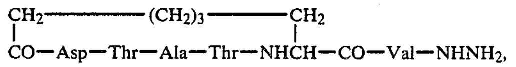

to which 0.63 ml of 4N hydrogen chloride was added while cooling the reaction system at −40° C. Then, 0.63 ml of isoamyl nitrite was added at −30° C. Since the hydrazine test gave a negative result 30 minutes later, 353 μl of triethylamine was added while cooling the reaction system at −70° C. so that the mixture was neutralized. The resulting mixture was added with 1.199 g of PF(9–37)-MBHA resin, followed by a further addition of 180 μl of triethylamine. The resulting mixture was stirred at 4° C. for 24 hours. After completion of the reaction, the reaction mixture was subjected to suction filtration, washed with 10 ml of DMF and dried under reduced pressure, thereby obtaining 1.27 g of desalanyl-[$Asu^{2,7}$]-protected-h-CGRP(3–37)-MBHA resin.

The above-described cyclic PF(3–8) [10] was prepared in the following manner.

(3) Cyclic protected PF(3–8):

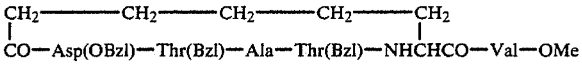

[8]

Dissolved in 40 ml of pyridine was 3.2 g of Boc-Asp(OBzl)-Thr(Bzl)-Ala-Thr(Bzl)-Asu-Val-OMe [7], to which 7 equivalents of p-nitrophenyl trifluoroacetate were added. The resulting mixture was stirred at 45° C. for 3 hours. After distilling off pyridine, ether was added and the resulting precipitate was collected. Thirty milliliters of TFA were added to the precipitate to remove Boc. TFA was then distilled off, followed by an addition of ether. The resulting precipitate was collected. It was dissolved in 70 ml of DMF. The thus-obtained solution was thereafter added dropwise to 2 l of pyridine of 45° C. The resulting mixture was stirred at 50° C. for 7 hours and then at room temperature overnight. Pyridine was distilled off from the reaction mixture under reduced pressure and the residue was extracted with 400 ml of chloroform to obtain the cyclic protected PF(3–8) [8]. Yield: 2.62 g.

(4) Cyclic PF(3–8):

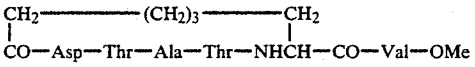

[9]

To 2.67 g of the cyclic protected PF(3–8) [8], 1 ml of anisole was added. While cooling the resulting mixture at 0° C., 15 ml of anhydrous hydrogen fluoride was added. The thus-prepared mixture was stirred for 1 hour. After the reaction, anhydrous hydrogen fluoride was distilled off under reduced pressure. The residue was washed with ether to obtain 1.75 g of white powder. The white powder was dissolved in 10 ml of DMF, followed by an addition of 10 ml of 0.1M acetic acid. The resulting mixture was then charge in a column (3.2 x 32 cm) of CHP-20 which had been filled with 0.1M acetic acid containing 20% DMF. The column was subjected to gradient elution with a linear concentration gradient of from 500 ml of 0.1M acetic acid containing 20% of DMF to 500 ml of 0.1M acetic acid containing 66% of DMF. The eluate was fractionated 14.8 ml by 14.8 m;. The 54th–63rd fractions were pooled and concentrated to dryness, thereby obtaining the cyclic PF(3–8) [9] as white powder.

Yield: 670 mg.

Melting point: 154°–160° C.

Amino acid analysis data: Asp 0.98 (1), Thr 1.90 (2), Ala 1, Val 0.96 (1), Asu 1.07 (1).

Mass spectrum: 673 ($M^+$) (calculated: 672.71).

(5) Cyclic PF(3–8):

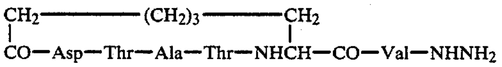

[10]

Dissolved in 6 m; of DMF was 404 mg of the cyclic PF(3–8) [9], followed by an addition of 0.8 ml of $NH_2$ *$NH_2$*.$H_2O$. The resulting mixture was stirred overnight. After the reaction, DMF was distilled off under reduced pressure, the residue was dissolved in 4 ml of water, and charged in a column (2.8×11.5 cm) of CHP-20. The column was subjected to gradient elution with a linear concentration gradient of from 300 ml of 0.1M acetic acid containing 10% of acetonitrile to 300 ml of 0.1M acetic acid containing 40% of acetonitrile. The eluate was fractionated 7.6 ml by 7.6 ml, and the 17th–20th fractions were pooled and lyophilized to obtain the cyclic PF(3–8) [10] as white powder. Yield: 85 mg.

Figure 8:
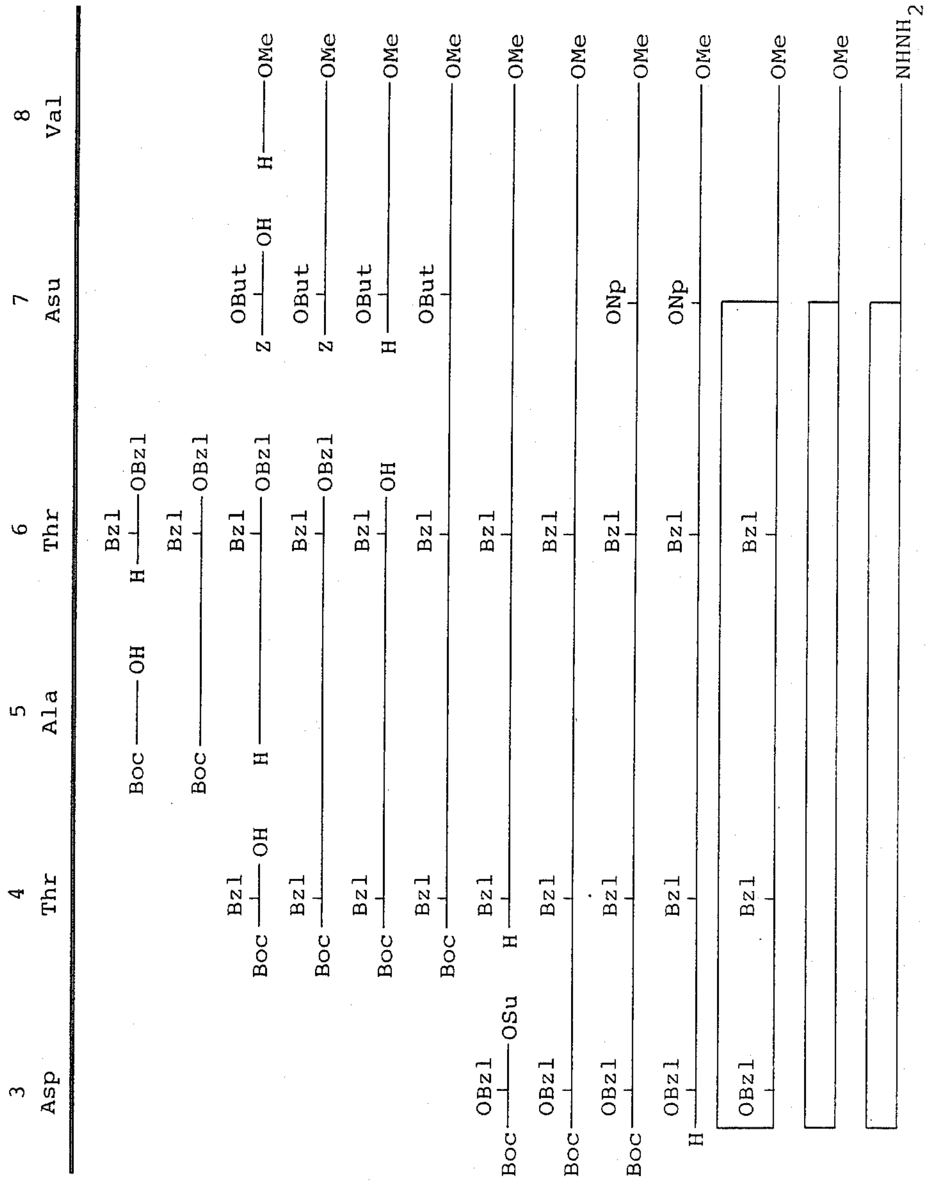
FIG. 8 is a flow chart for the preparation of the peptide fragment (3–8).

The above-described Boc-Asp(OBzl)-Thr(Bzl)-Ala-Thr(Bzl)-Asu-Val-OMe [7]was prepared in accordance with the process shown in the flow chart for the peptide fragment (3–8) of FIG. 8. Incidentally, the intermediate peptide fragments in the course of the preparation had the following physical and chemical properties.

(1) PF(5–6): Boc - Ala - Thr(Bzl) - OBzl.

TLC: $Rf_4$=0.93.

Melting point: 89°–95° C.

Amino acid analysis: Thr 1.00 (1), Ala 1.

$[\alpha]_D^{26.5}$: 10.75 (c=0.99, DMF).

(2) PF(4–6): Boc - Thr(Bzl) - Ala - Thr(Bzl) - OBzl

TLC: $Rf_4$=0.73.

Melting point: 92°–94° C.

Amino acid analysis: Thr 1.97 (2), Ala 1.

$[\alpha]_D^{26.5}$: 5.42 (c=1.00, DMF).

(3) PF(4–6): Boc - Thr(Bzl) - Ala - Thr(Bzl) - OH.

TLC: $Rf_4$=0.32.

Melting point: 54°–58° C.

Amino acid analysis Thr 1.86 (2), Ala 1.

$[\alpha]_D^{26.5}$: 24.20 (c=1.03, DMF).

(4) PF(7–8): Z - Asu(OBut) - Val - OMe.

TLC: $Rf_4$=0.90.

Melting point: oily at room temperature.

(5) PF(7–8): H - Asu(OBut) - Val - OMe.

TLC: $Rf_4$=0.25.

Melting point oily at room temperature.

(6) PF(4–8) Boc - Thr(Bzl) - Ala - Thr(Bzl)-Asu(OBut) - Val - OMe.

TLC: $Rf_4$=0.64.

Melting point: 107°–113° C.

Amino acid analysis Thr 1.83 (2), Ala 1, Val 1.05 (1), Asu 1.18 (1).

$[\alpha]_D^{26.5}$: 5.46 (c=1.03, DMF).

(7) PF(3–8): Boc - Asp(OBzl) - Thr(Bzl) - Ala -Thr(Bzl) - Asu - Val - OMe [7].

TLC $Rf_5$=0.58

Amino acid analysis: Asp 1.04 (1), Thr 2.04 (2), Ala 1, Val 1.06 (1), Asu 1.25 (1).

Having now fully described the invention, it will be apparent to one of ordinary skill in the art that many changes and modifications can be made thereto without departing from the spirit or scope of the invention as set forth herein.

What is claimed as new is secured by Letters Patent is:

1. A peptide represented by the following formula:

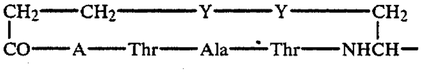

—CO—Val—Thr—His—Arg—Leu—Ala—Gly—Leu—Leu—

-continued

—Ser—Arg—Ser—Gly—Gly—B—Val—Lys—C—Asn—Phe—

—Val—Pro—Thr—Asn—Val—Gly—Ser—Lys—

—Ala—Phe—$NH_2$ wherein Y means a sulfur atom or methylene group, A stands for Asp or Asn, B denotes Val or Met and C is Asn or Ser, or a salt thereof.

2. The peptide as claimed in claim 1, which is a peptide represented by the following formula:

```
CH2——————CH2——————S——————S——————CH2
|                                |
CO——Asp——Thr——Ala——Thr——NHCH—
```

—CO—Val—Thr—His—Arg—Leu—Ala—Gly—Leu—Leu—

-continued

—Ser—Arg—Ser—Gly—Gly—Val—Val—Lys—

—Asn—Asn—Phe—Val—Pro—Thr—Asn—Val—

—Gly—Ser—Lys—Ala—Phe—$NH_2$, or a salt thereof.

3. The peptide as claimed in claim 1, which is a peptide represented by the following formula:

```
CH2——CH2—CH2—CH2——CH2
|                 |
CO—Asp—Thr—Ala—Thr—NHCH—CO—Val—Thr—His—
```

—Arg—Leu—Ala—Gly—Leu—Leu—Ser—Arg—Ser—Gly—

—Gly—Val—Val—Lys—Asn—Asn—Phe—Val—Pro—Thr—

—Asn—Val—Gly—Ser—Lys—Ala—Phe—$NH_2$,

* * * * *